United States Patent
De Oliveira et al.

(10) Patent No.: US 9,542,841 B2
(45) Date of Patent: Jan. 10, 2017

(54) APPARATUS AND METHOD EMPLOYING SENSOR-BASED LUMINAIRES TO DETECT AREAS OF REDUCED VISIBILITY AND THEIR DIRECTION OF MOVEMENT

(71) Applicant: PHILIPS LIGHTING HOLDING B.V., Eindhoven (NL)

(72) Inventors: Talmai Brandão De Oliveira, Peekskill, NY (US); Jianfeng Wang, Ossining, NY (US); Dave Alberto Tavares Cavalcanti, Mahopac, NY (US)

(73) Assignee: PHILIPS LIGHTING HOLDING B.V., Eindhoven (NL)

( * ) Notice: Subject to any disclaimer, the term of this patent is extended or adjusted under 35 U.S.C. 154(b) by 0 days.

(21) Appl. No.: 14/900,216

(22) PCT Filed: Jun. 6, 2014

(86) PCT No.: PCT/IB2014/062005
§ 371 (c)(1),
(2) Date: Dec. 21, 2015

(87) PCT Pub. No.: WO2014/207592
PCT Pub. Date: Dec. 31, 2014

(65) Prior Publication Data
US 2016/0148506 A1    May 26, 2016

Related U.S. Application Data

(60) Provisional application No. 61/839,472, filed on Jun. 26, 2013.

(51) Int. Cl.
G08B 21/00    (2006.01)
G08G 1/09    (2006.01)
(Continued)

(52) U.S. Cl.
CPC .............. *G08G 1/09* (2013.01); *G08G 1/0116* (2013.01); *G08G 1/0133* (2013.01);
(Continued)

(58) Field of Classification Search
CPC ....................................................... G08G 1/09
(Continued)

(56) References Cited

U.S. PATENT DOCUMENTS

| 2005/0072907 A1 | 4/2005 | Pallaro |
| 2008/0007429 A1 | 1/2008 | Kawasaki |

(Continued)

FOREIGN PATENT DOCUMENTS

| CN | 2648761 Y | 10/2004 |
| CN | 201412765 A | 2/2010 |

(Continued)

OTHER PUBLICATIONS

Wu, H. et al , "Sensor Fusion using Dempster-Shafer Theory II: Static Weighting and Kalman Filter-like Dynamic Neighting," in Proceedings of IEEE Instrumentation and Measurement Technology Conference, 2003.

*Primary Examiner* — Jeffery Hofsass (57) ABSTRACT

A method and system that relies on visibility detectors deployed on luminaires in outdoor lighting networks (OLNs) to independently treat and consolidate the sensed data in a fault-tolerant manner. By communicating with neighboring luminaires and/or with a centralized server, the invention is able to identify the position and direction of movement of areas of reduced visibility (e.g. fog). This information can then be used to alert drivers who are approaching the identified area.

23 Claims, 4 Drawing Sheets

(51) Int. Cl.
 *G08G 1/01* (2006.01)
 *G08G 1/0967* (2006.01)
 *G01N 21/53* (2006.01)

(52) U.S. Cl.
 CPC ..... *G08G 1/0141* (2013.01); *G08G 1/096758* (2013.01); *G08G 1/096783* (2013.01); *G01N 21/538* (2013.01); *Y02B 20/72* (2013.01)

(58) Field of Classification Search
 USPC ................... 340/901–905, 933, 601, 602
 See application file for complete search history.

(56) References Cited

U.S. PATENT DOCUMENTS

2010/0262297 A1   10/2010   Shloush
2014/0029790 A1    1/2014   Gallen

FOREIGN PATENT DOCUMENTS

| CN | 102622892 A | 8/2012 |
|---|---|---|
| EP | 1521226 A1 | 4/2005 |
| EP | 1546464 A1 | 6/2005 |
| KR | 2009100174 A | 9/2009 |
| KR | 2010094226 A | 8/2010 |
| WO | 2012140152 A1 | 10/2012 |
| WO | 2013042017 A1 | 3/2013 |

APPARATUS AND METHOD EMPLOYING SENSOR-BASED LUMINAIRES TO DETECT AREAS OF REDUCED VISIBILITY AND THEIR DIRECTION OF MOVEMENT

CROSS-REFERENCE TO PRIOR APPLICATIONS

This application is the U.S. National Phase application under 35 U.S.C. §371 of International Application No. PCT/IB2014/062005, filed on Jun. 6, 2014, which claims the benefit of U.S. Provisional Patent Application No. 61/839,472, filed on Jun. 26, 2013. These applications are hereby incorporated by reference herein.

The present invention is directed generally to employing outdoor lighting networks (OLNs) to detect and provide information related to areas of reduced visibility, and in particular information related to fog conditions. More particularly, various inventive methods and apparatus disclosed herein relate to deploying fog sensors on luminaires in such OLNs to independently treat and consolidate the sensed data in a fault-tolerant manner. By communicating with neighboring luminaires and/or with a centralized server, fog positioning and direction of movement is identified. Further, the present invention provides a means to disseminate fog detections to thereby alert drivers who may be approaching the fog covered area.

As is well known in the art, outdoor lighting poles are natural choices to place surveillance cameras to monitoring streets, parking lots, parks, and other outdoor areas. OLNs are thus used not only to control and manage outdoor lighting units, but to transmit data from cameras installed on lighting poles to monitoring centers. Further, the lighting units employed may also include lamps, video/image sensors, data storage, and communication and control modules that are connected with a centralized server directly or through other lighting units. Such an OLN system is described in co-pending patent application entitled "IMAGING SERVICE USING OUTDOOR LIGHTING NETWORKS" filed on Sep. 22, 2011 in the US Patent and Trademark Office and afforded Ser. No. 61/537,945, the contents of which are incorporated by reference, herein.

Figure 1:
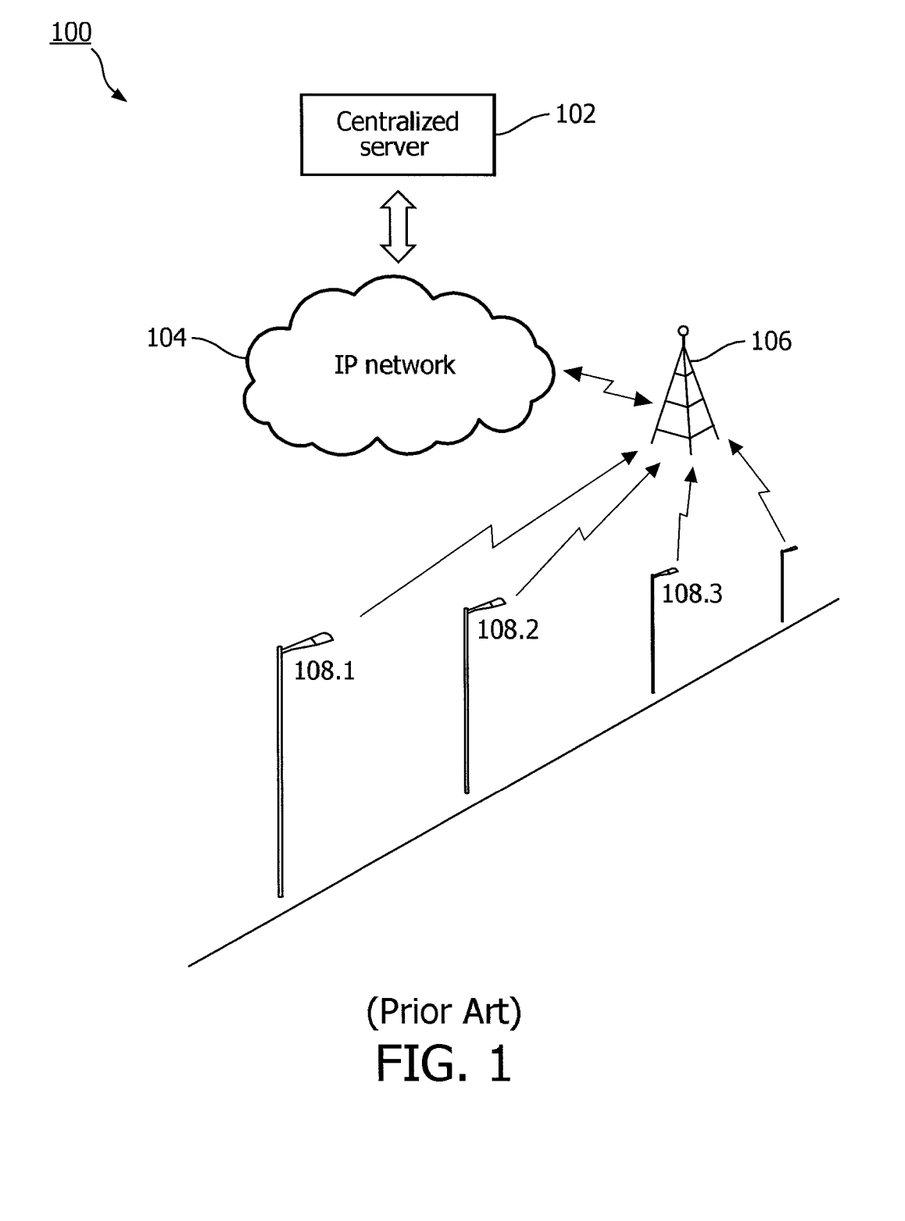
FIG. 1 depicts a prior art outdoor lighting network.

An example of a conventional outdoor lighting network 100 is shown in FIG. 1. As illustrated therein light points or luminaires 108.1-108.3 are in communication with an antenna tower 106 which, through an IP network 104, is in communication with a centralized server 102. It should be noted that various other means of communication are contemplated by the invention. These include power line communication or Radio Frequency (RF) mesh network of the light points. Further, the network connecting to the Centralized Server 102 may be wired, wireless and/or cellular networks. Still further, The Centralized Server 102 may also communicate with one or more light points directly if that light point is reachable through a cellular network. Still further, it is contemplated by the invention that the light points of the OLN may communicate directly with each other without requiring the tower structure 106 or the centralized server 102 depicted in FIG. 1. Such communication can be conducted by various means that are well-known in the art, to include wireless communication, wired communication (e.g., over power lines) and visual light communication.

The current invention relates to the field of intelligent sensor-enabled luminaires capable of sensing the physical world, performing diverse calculations and manipulation of the sensed data pertaining to fog detection, and transmitting information to processors, controllers and mobile devices. These would include nearby vehicles, autonomous devices (e.g., self-driving cars and unmanned aerial vehicles), or internet-connected mobile devices (e.g., smartphones and tablets), as well as centralized data warehouses with internet-based user interfaced applications. Particularly, the current invention relates to:

1. Testing and validating the input value obtained from the fog sensors, to allow for a more reliable input
2. Identifying fog positioning as well as the direction of movement (if it exists)
3. Alerting drivers and/or other autonomous devices of unsafe conditions due to fog.

Unlike tornadoes or thunderstorms, fog is a somewhat passive weather phenomenon. Still, it's known to catch motorists by surprise. Fog tends to form on clear, cool nights when moist air accumulates slightly above the ground or water. This air is mixed during the night to form condensation, which dissipates as the sun rises. The extreme variability of fog, especially in its density and location, make it difficult for motorists to perceive and react quickly. Since light is refracted and deflected by the water droplets of the fog, this event is not at all limited to early mornings, and in fact can affect both day and night driving conditions.

Fog is measured by visibility in miles, and is considered severe when visibility is ¼ mile or less. The foggiest location in the United States is located at Cape Disappointment, Wash., with 106 severe fog days per year. On the east coast, it is the city of Eastport, Me. that takes the prize with 65 days. In inland areas, the foggiest location is Elkins, W. Va. with 81 days. By way of comparison, further south in Tampa Bay, Fla., the average is of 22 days. In northern Utah, super-cooled fog (<32 F) can persist in mountain valleys for weeks [http://ops.fhwa.dot.gov/weather/best_practices/CaseStudies/025.pdf].

The often dramatic change in visibility, as well as the slowing of traffic, is what has led to many multi-car pileups with injuries and even deaths. Fog prediction, however, is no easy feat due to the variability in density, location, dissipation rates and area of coverage at a given point in time. Drivers who are most likely to be involved in fog-related crashes are residents of the neighboring counties—older than 20 but younger than 30—driving during the morning commute hours and traveling on local and county roads in rural locations. Curiously, most fog-related crashes occur when the vehicle is traveling straight ahead.

The general conclusion from the National Transportation Safety Board (NTSB) regarding investigations of major fog incidents was that they occurred because drivers did not maintain uniform reduced speeds during times of limited visibility. Sadly, maintaining uniform reduced speeds does not guarantee that a crash will be avoided.

When fog does form, accurate real-time information on the presence and density is necessary for effective traffic control and initiation of safety measures. Currently, the National Oceanic and Atmospheric Administration (NOAA) Weather Wire Service collects all types of weather data and offers advisories. Unfortunately, this is still not enough to reduce the number of accidents. Generally, fixed message signs are used to identify fog-prone areas. However, since they represent the prevailing conditions only for a portion of the year, drivers may even ignore them. Therefore, they tend to be ineffective because the traveling public considers them to be irrelevant. Altogether, the principal form of fog detection continues to be the personal observation by the State police.

Many states have formally deployed detection and warning systems, as well as integrated visibility/weather and motorist warning systems. Investments range from around $2-$4 million (see, e.g., http://www.cutr.usf.edu/research/fog.pdf and http://www.gtri.gatech.edu/casestudy/happy-motoring-safer-interstate-highway), and a complete solution (with visibility sensors, speed detectors, electronic signage and cameras to detect congestion) can reach upwards to the $12 million range (http://gs.flir.com/uploads/file/case-studies/case-study_caltrans-fog.pdf). The benefits of these systems, however, have not been clearly documented, and most states simple resort to driver awareness campaigns as the most cost-effective measure to reduce these types of crashes.

The highest contributing factor to such high investment amounts appears to be the electronic signs and the required infrastructure to connect them (often in the $2+ million range). The fog sensing devices, on the other hand, are readily available at much more accessible prices. Forward scatter visibility sensors, for example, range from $5 k to $8 k per unit.

Forward scatter technology measures the extinction coefficient—the sum of the absorption and scattering properties of light in the atmosphere. It does this by transmitting a narrow beam of light from a light-emitting diode (LED), which then scatters particles of light into a receiver. This receiver has an infrared detector that produces electrical energy equal to the amount of light received by the detector.

The transmitter and receiver are aimed toward each other at an angle. If the air is clear, the transmitted infrared beam will pass by the receiver and no light will be detected. If the air becomes hazy or if precipitation is present, the beam will be scattered. The receiver will detect some of the scattered infrared light, proportional to the amount of haze or precipitation. The input to the receiver passes through an infrared filter to reduce the effects of other light. The sensors also incorporate several techniques that reduce the maintenance needed and ensure that the sensor remains reliable between maintenance visits (e.g., see http://tidesandcurrents.noaa.gov/publications/Technical_Report_NOS_CO-OPS_055.pdf).

Assuming a fog-prone area is known, such forward scatter visibility sensors can be incorporated with and/or in communication with luminaires. Accordingly a cheaper alternative can be reached for fog warning systems, as long as a fault tolerant distributed system can be developed to interconnect the sensors and that reliable, high detection rates can be obtained.

The current invention overcomes the problems in the prior art and provides cost savings while maintaining accuracy. Further, the current invention attains increased functionality with respect to communicating both raw data and fog analysis results.

In Various Embodiments of the Invention, a System is Described which Comprises the Following Components:

1. A smart lighting device capable of communicating with neighboring devices through various types of communication interfaces, to include wired, wireless and visual light communication means. Devices are also capable of store-and-forward, that is, they can receive data from neighbors, and at a later time forward that information on.
2. Smart lighting devices can communicate and inform nearby cars and autonomous devices of hazards. In addition, these may have applications that continuously poll a centralized server for data. The electronics in the car, for example, may choose to display the information for the driver, or take an action on its own, such as turn on the fog light, engage the all-wheel-drive, enable stability control, or emphasize maximum recommended driving speeds. An autonomous drone may increase its elevation and turn on warning LED's to signify a severe scenario. Finally, devices can also communicate with each other, forwarding data and exchanging information. In one embodiment, an individual vehicle has fog detection capability. When it detects fog, it transmits the information to one or more luminaires/poles using for instance dedicated short-range communications (DSRC) based radios, or even using the drivers' smartphone to connect to the internet. The Luminaires/poles then transmit the fog information to the central server and/or back propagate the alert to other vehicles in the vicinity of the vehicle so that they can take preventive actions to avoid a potential accident.
3. A fog sensor unit is attached to the lighting device. These sensors detect fog, albeit with possible failures. Many prior art sensors have measurement ranges from 33 feet to 20 miles, with accuracy in the ±10% range. In practice, however, fog-prone zones are densely monitored, so it can be safely assumed that such sensors are within the lower values of the range. In a further embodiment of the invention, some overlap exists between sensors to account for varying sensing ranges. In a still further embodiment, LED luminaires integrate fog sensing functionality by leveraging the self-embedded LED and processing power (e.g., to employ forward scatter technology).
4. A centralized server with processor(s) and database(s) where the data is sent, processed and stored.
5. Certain components of the lighting network (denominated gateways) may rely on fixed infrastructure (wireless LTE, WiMAX, or other wired mechanisms such as fiber optics) to communicate with the centralized server.
6. The centralized server has a detailed map of city; which may include GPS locations of luminaires, as well as direction of traffic (car) flow in each street, and max/min speed limits.

In Further Embodiments of the Invention, a Method is Described which Comprises the Following Capabilities:

1. A data input treatment and validation mechanism that is capable of dealing with uncertainties due to sensor disparity, as well as sensor failures. This can be implemented as either a distributed mechanism (in that it is executed individually by a "smart" luminaire (as described below) and then communicated with neighboring devices), or a centralized mechanism (where all information is first routed to a centralized server);
2. A fog positioning and movement direction mechanism that is performed through a distributed aggregation protocol between neighboring luminaires;
3. A transmission protocol that is capable of alerting drivers who are in severe fog zones as well as those that are still in areas with lower or no fog whatsoever. This can occur between lighting devices and vehicles, between vehicles themselves, as well as from the centralized server to the vehicle.

The advantages, nature, and various additional features of the invention will appear more fully upon consideration of the illustrative embodiments to be described in detail in connection with accompanying drawings wherein like reference numerals are used to identify like element throughout the drawings.

It is to be understood that these drawings are solely for purposes of illustrating the concepts of the invention and are not intended as a definition of the limits of the invention. It will be appreciated that the same reference numerals, possibly supplemented with reference characters, where appropriate, have been used throughout to identify corresponding parts.

The following discussion of the invention will primarily be directed to fog detection. However, the invention is not so limited as the invention can be employed for other phenomenon in which visibility is affected—in particular, visibility of drivers. These may include smog, smoke from fires, dust storms, dust/debris in proximity to a tornado vortex. In additional embodiments of the invention, light poles are equipped with flood sensors at their base. Once flooding is detected at a pole, that information could be forwarded to other poles and/or a centralized server. In this manner nearby poles could confirm direction of growth or movement of the flood affected area. Thus the present invention is capable of providing information related to weather phenomenon that can be used to alert governmental agencies as well as individuals and vehicles that are in or approaching the affected areas.

Figure 2:
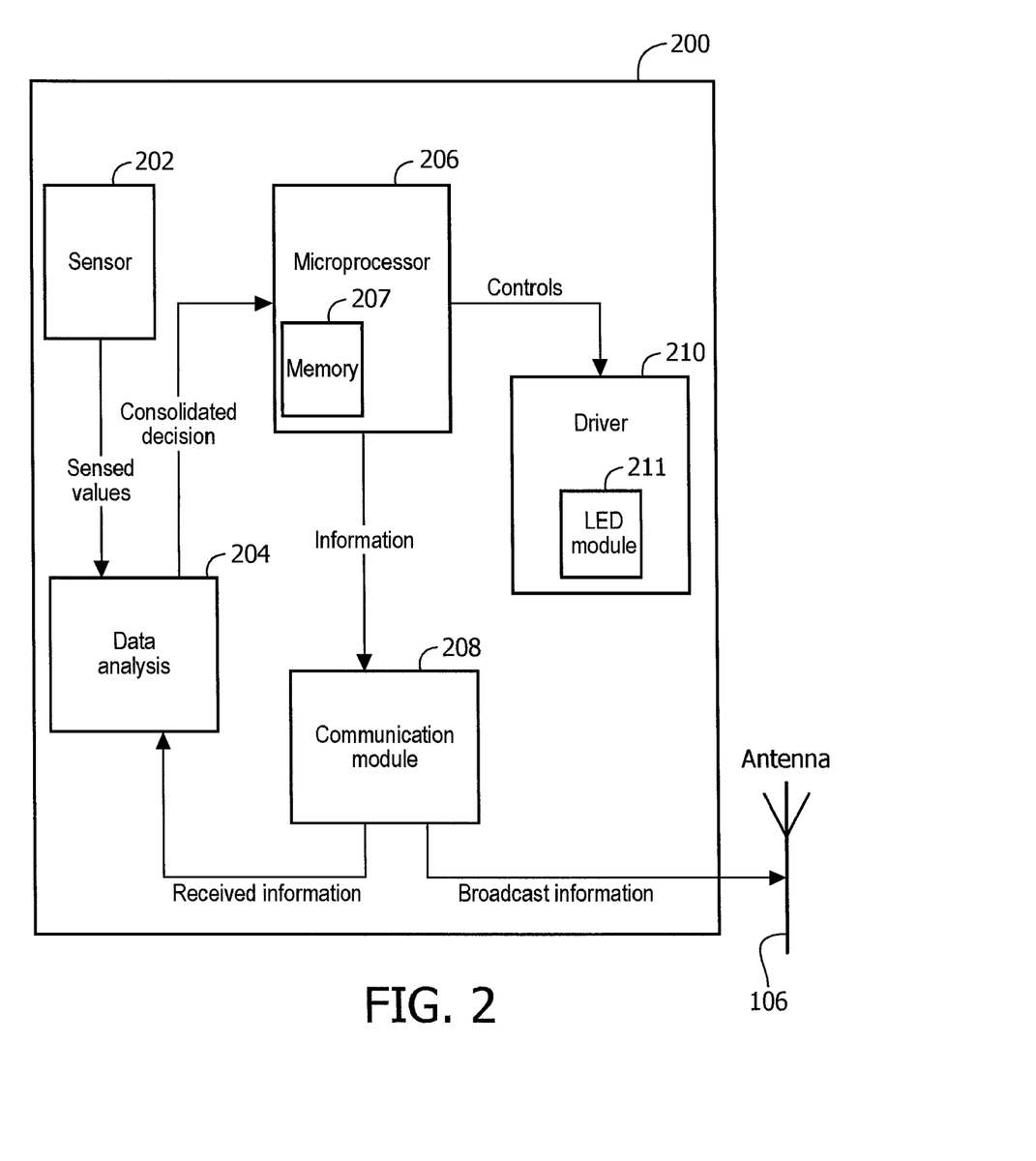
FIG. 2 illustrates an exemplary smart luminaire of an embodiment of the present invention.

FIG. 2 illustrates an exemplary smart luminaire 200 of the present invention. As illustrated, the luminaire comprises a sensor 202 for attaining sensed values that are provided to a data analysis module 204. A microprocessor 206, which contains a memory 207, receives results attained by the data analysis module 204. The microprocessor 206 provides information to a communication module which is capable of transmitted this information (as described below) via an antenna 106. The microprocessor 206 also controls the luminaire driver 210, which in the particular embodiment illustrated, includes an LED Module 211. As illustrated, luminaire 200 is also capable of receiving information via antenna 106 which is received by the communication module 208 and provided to the data analysis module 204 in making the decisions provided to the microprocessor 206.

In the embodiment illustrated in FIG. 2, a "smart luminaire" is depicted. In additional embodiments of the invention, one or more luminaires may not contain all of these components or associated functionality. That is, a particular luminaire may only contain a sensor and a communication module; whereby at least some of the additional functionality described above may reside in another luminaire or in a management module. Alternatively, a particular luminaire may only contain a communication module, thereby enabling a communication link between modules. Thus, it is envisioned that a distributed functionality exists whereby the features described above may be implemented in one or more various components of the system.

Data Input Treatment and Validation Mechanism

Each sensor device 202 continuously senses fog environmental data and outputs a value which measures how "foggy" the environment is. As noted above, the actual criterion being measured is how visibly obstructed one's view is that is due to various environment factors. The term "foggy" will hence be used to collectively refer to the level of that obstruction.

Without lack of generality, the following discussion assumes that this value is numeric. Two things may be associated with that value: 1) the sensor may be faulty or needing maintenance. Therefore, the luminaire needs to be able to identify this scenario; 2) since luminaires are placed in different geographical locations, different neighboring devices may very likely identify different numerical values.

It should be noted that two events are identified because the solution to the former often relies on the communication and aggregation of measured values from nearby neighbors. Existing methods can take the average, mean, or use additional statistical analysis to reach a "single value" from the combination of many sensors. However, due to the extreme variability of fog, this is no easy feat. In fact, if it existed, current solutions would have shown drastic reduction in levels of accidents. Reports indicate that technologies probably cannot provide effective solutions if problematic locations are dispersed and scattered. Cheaper, distributed solutions, such as those described herein with respect to the present invention, would be much more effective. That is, the current invention discloses a process to better facilitate the validation of the measured values, through a mechanism that embraces uncertainty and subjectivity. In the following described embodiment of the invention, this is obtained through a 2-step process:

Step 1 (Mapping):

Linguistic classes of fog levels are first defined. For example, "no fog", "low visibility", "severe", "very dangerous" and so forth. These are pre-defined and associated with ranges of values by a fog expert beforehand. If the measured value from a fog sensor is within the range of any of the classes, then it is said to "belong" to the class with a certain amount of membership. This is actually a mapping that transforms the numerical single value into a tuple of values containing the class, and a percentage of membership. The combination of all percentage values should equal to 100%. What this means is that, the subjective perception of the fog sensor will be completely defined by the sum of all membership classes. Consequently, in the present invention, classes should overlap, and will contain both single elements as well as combination of elements.

By way of example, assuming that there are 2 linguistic classes defined {"no fog", "some fog"}. The membership classes would then contain the single elements {"no fog"} and {"some fog"}, as well as the combination elements {"no fog"+"some fog"}. The final set of classes used during the mapping step will allow for 3 different options, which are: {"no fog", "no fog"+"some fog", "some fog"}.

At the end of step 1, each individual luminaire will have its own set of tuples <class, membership> which will most likely vary from one to the other. Thus by way of example, "membership" may be expressed as a percentage. Accordingly, a luminaire may arrive at the conclusion of: [no fog, 2%], [some fog, 60%]. It is also likely that a luminaire may determine after this mapping step, that it belongs to multiple classes with high membership levels. This is acceptable and even welcomed. While this introduces uncertainty, it also resembles how human perception works—very subjective and depending on multitude of factors.

Step 2 (Decision and Validation):

According to the present invention, for the decision phase the luminaire will behave differently depending on whether it has neighboring luminaires to which it is capable of communicating with or not. In one embodiment, luminaires can detect whether they have neighbors by listening to periodical "HELLO" messages sent, and/or as told by the centralized server. Once this is determined:

a) If the luminaire does not have any neighbors, then it will decide on the class with the highest membership. This is a simple comparison between classes. If two (or more) classes have the same membership, the class chosen should always prefer combination elements.

b) If the luminaire has neighbors, then it executes a supplemental step—and will merge its decision with that of its neighbors based on any number of Evidential Reasoning algorithms previously published. By way of example such publications include: G. Shafer, A mathematical theory of evidence. Princeton university press, 1976; B. Marhic, L. Delahoche, C. Soleau, A.-M. Jolly-Desodt, and D. Menga, "Detection of abnormal sensor behaviour using tbm," in Proceedings of the Workshop on the Theory of Belief Function, 2010; and H. Wu, M. Siegel, and M. Siegel, "Sensor fusion using dempster-shafer theory," in Proceedings of IEEE Instrumentation and Measurement Technology Conference, pp. 21-23, 2002. What these algorithms allow for is the capability of merging different tuples while being able to handle contradictions. For example, any of these algorithms would allow the merging of a luminaire that is 90% sure that "no fog" occurred with a luminaire that is "90%" that "severe fog" occurred. At the end of this step, each luminaire would have contacted its neighbors and obtained, besides their individual decision, a final merged perception tuple of <class, membership>.

At this point in time, each individual luminaire will have either a single decision (2a above) or a single decision and a merged perception (2b). This information is saved in the luminaires' memory, where a history of time-based decisions and perceptions can be analyzed. In additional embodiments of the invention, this information is also transmitted to the centralized server through the available gateway. By looking at the history, a luminaire (or the centralized server) can identify individual luminaire fog-sensor related failures, as well as reach a localized consensus on the fog-detection event. At the end of step 2, each luminaire will have a single decision which linguistically measures it's perception of the fog environmental data.

Fog Position and Direction of Movement Identification

In an embodiment of the present invention, single linguistic decisions are analyzed from each luminaire; and, by analyzing the decisions of all luminaires within a certain area; the fog position, any recent changes in its size, and its direction of movement is identified. The analysis can be done either in a centralized manner—by transmitting all decisions to the centralized server, or through a distributed manner—by nodes reaching a localized consensus using group membership protocols. Without loss of generality, examples related to the centralized solution are provided below.

Fog Position Pinpointing:

In this Embodiment, a Centralized Server is Provided Wherein the Centralized Server Possesses the Following Information:

a) The exact location of the luminaires. This could have been obtained in the commissioning phase, for example, by using handheld GPS-enabled devices and later stored in an accessible database. In addition, the location of luminaires could be determined through localization techniques applied within the OLN or by means of GPS devices installed in the luminaires themselves.

b) A mapping of GPS locations to streets, and capacity of identifying sequences of luminaires. That is, that a certain luminaire comes before or after another, and which luminaires are neighbors of one another.

c) The direction of traffic flow on each street.

Figure 3A:
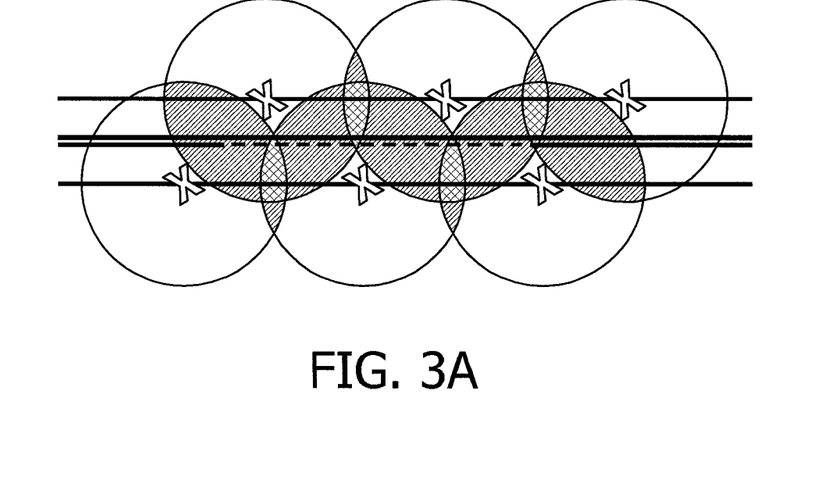
FIGS. 3A and 3B illustrate obtained scanning results from multiple scanners and how this data is combined.

Each luminaire will transmit to the centralized server its decision (obtained in the phase described above). The centralized server will then execute a conflict resolution and merging mechanism that also relies on, e.g., Evidential Reasoning on groups of neighboring nodes. The position is determined by a step-wise merging of the decisions from neighboring luminaires. A simple graphical example is provided in FIG. 3A, where each indicated "X" represents a luminaire that is illustrated as being at the center of an area being monitored. For the sake of simplicity, these areas are indicated as being circles. However, the invention is not so limited as terrain features, structures, trees, etc. would typically result in an asymmetric area. Within each area, a decision is determined and depicted as various shaded mappings, with darker shading indicating a detected higher incidence of fog. The results are then overlaid as indicated in the figure.

Figure 3B:
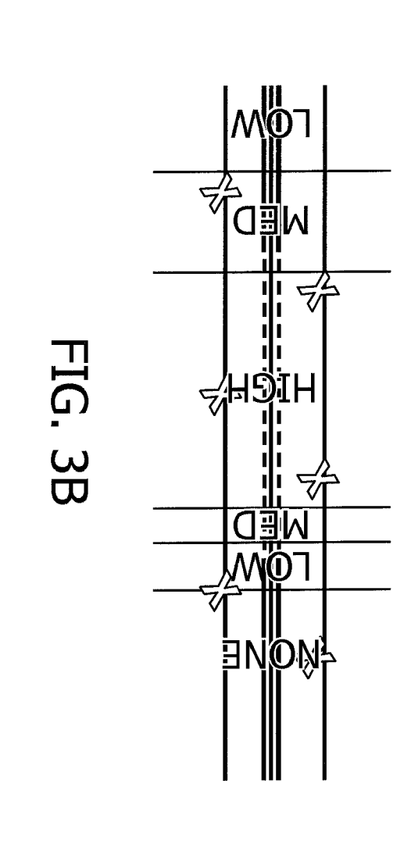

Fog positioning can be thus be inferred with confidence intervals. That is, the information illustrated in FIG. 3A would lead the system to infer which areas have higher or lower chances of fog. The result of this analysis is depicted in FIG. 3B.

Fog Movement Direction Identification:

To determine the direction of fog movement, a series of time-stamped positing results would be compared. That is by way of example, detection results from a plurality of individual luminaires are combined such that the history of such results (e.g., time and location of luminaires involved) can be used to determine the direction of fog movement. By analyzing the direction (or lack thereof) of how each inferred area changes, the system is capable of determining both direction and speed of movement.

Early-Alert Mechanism of Unsafe Conditions to Drivers

In a further embodiment of the invention, a transmission mechanism is provided that is capable of alerting drivers who are in severe fog zones as well as those that are still in areas with lower or no fog whatsoever.

With the information obtained from the previous two phases, the system is capable of knowing where the fog is located with varying levels of certainty and severity. It also knows the movement direction and speed of the mass of fog. With this information, coupled with the previously established max/min speeds of car traffic, the early-alert mechanism works by back-propagating the information to luminaires established in outside zones.

Figure 4:
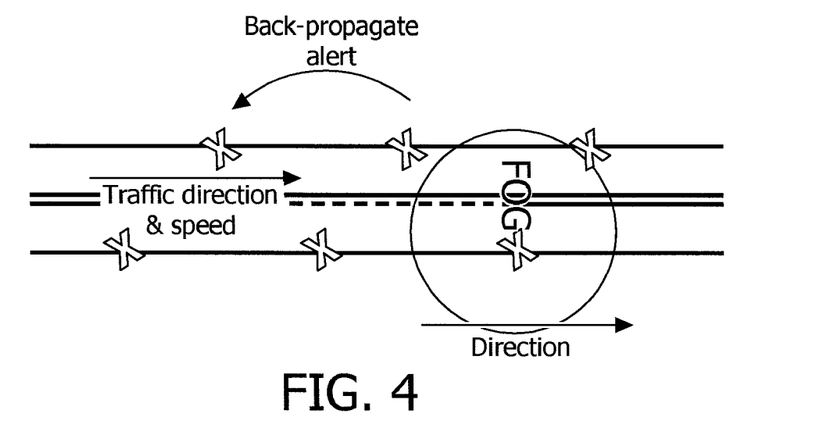
FIG. 4 illustrates the back propagation feature of an embodiment of the present invention.

Given the fog direction and speed, and given the traffic direction and speed, this invention is capable of calculating how far to back-propagate the alert. This feature of the invention is depicted in FIG. 4. In various embodiments of the invention, one or more luminaires are equipped to communicate directly with passing cars, and/or this information can also be displayed through an alert on the driver's smartphone or other networked device.

Figure 5:
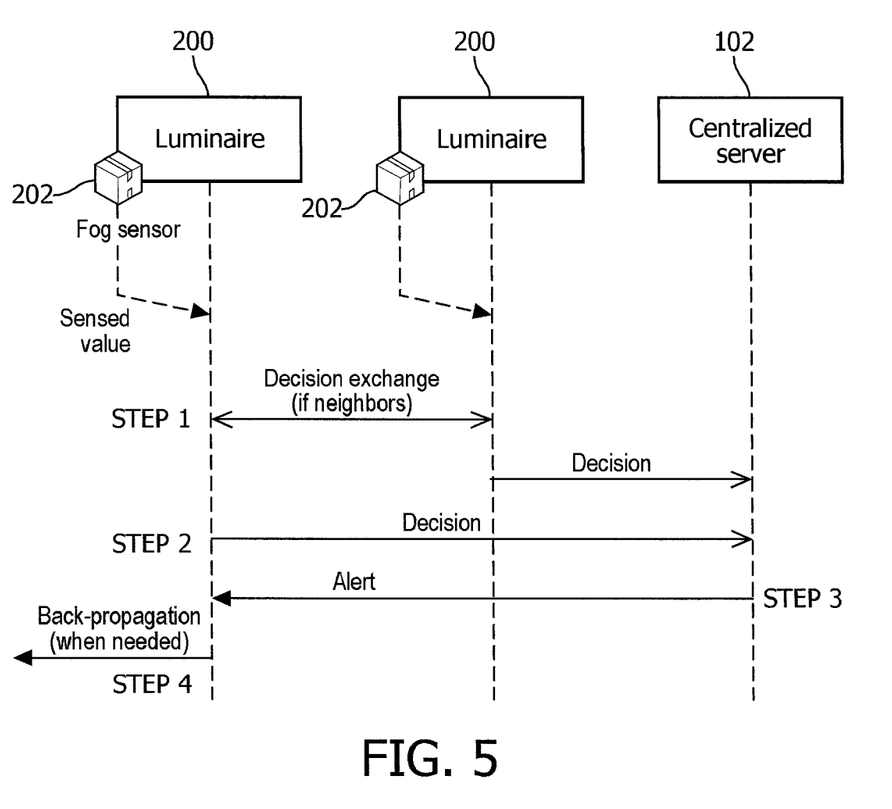
FIG. 5 is a flowchart illustrating communication paths in various embodiments of the invention.

FIG. 5 illustrates a flow chart of an embodiment of the invention. Once a luminaire receives the value from the fog sensor 202, step 1 is executed and a decision is made.

Depending on locality factors, the luminaire 200 may communicate with neighboring luminaires or directly with the centralized server 102 (at step 2). Finally, the server 102 pinpoints the fog position and movement direction, and alerts the appropriate luminaire(s) (at step 3). At step 4, this alerted luminaire 200 can then back-propagate when needed, and send the alert to the passing drivers.

As one skilled in the art would recognize, the terms processor, processing system, computer or computer system may represent one or more processing units in communication with one or more memory units and other devices, e.g., peripherals, connected electronically to and communicating with the at least one processing unit. Furthermore, the devices illustrated may be electronically connected to the one or more processing units via internal busses, e.g., serial, parallel, ISA bus, microchannel bus, PCI bus, PCMCIA bus, USB, etc., or one or more internal connections of a circuit, circuit card or other device, as well as portions and combinations of these and other communication media, or an external network, e.g., the Internet and Intranet. In other embodiments, hardware circuitry may be used in place of, or in combination with, software instructions to implement the invention. For example, the elements illustrated herein may also be implemented as discrete hardware elements or may be integrated into a single unit.

While there has been shown, described, and pointed out fundamental novel features of the present invention as applied to preferred embodiments thereof, it will be understood that various omissions and substitutions and changes in the apparatus described, in the form and details of the devices disclosed, and in their operation, may be made by those skilled in the art without departing from the spirit of the present invention. It is expressly intended that all combinations of those elements that perform substantially the same function in substantially the same way to achieve the same results are within the scope of the invention. Substitutions of elements from one described embodiment to another are also fully intended and contemplated. For example, any numerical values presented herein are considered only exemplary and are presented to provide examples of the subject matter claimed as the invention.

Hence, the invention, as recited in the appended claims, is not limited by the numerical examples provided herein.

What is claimed is:

1. A method for providing visibility alerts, said method using at least one Outdoor Lighting Network (OLN) comprising a plurality of lighting units at least two of which are in communication with each other, wherein a plurality of visibility detectors are each in communication with at least one of the lighting units, said method comprising:
   monitoring by each visibility detector a geographical area;
   receiving monitoring data from two or more of the visibility detectors;
   deriving a consolidated estimate of visibility conditions pertaining to a combined geographical area defined by the monitored geographical areas associated with two or more visibility detectors;
   determining direction and speed of an area of reduced visibility area using the consolidated estimate of visibility conditions; and,
   transmitting information pertaining to said estimated visibility conditions and/or area of reduced visibility.

2. The method of claim 1 wherein said deriving step comprises mapping from data received from each visibility detector to a set of tuples; wherein said tuples comprises membership classes that are associated with levels of obscured visibility.

3. The method of claim 2 wherein said tuples comprises a percentage membership associated with each class.

4. The method of claim 2 wherein said deriving step is performed by a centralized server; and wherein tuples from a plurality of light units are utilized in deriving the consolidated estimate.

5. The method of claim 3 wherein said deriving step is performed by a first light unit, the first light unit being in communication with a least one neighboring light unit which monitors at least part of the same geographical area as that being monitored by the first light unit;
   wherein said deriving step further comprises merging an estimate derived by the first light unit pertaining to the geographical area being monitored by the first light unit, with one or more estimates derived by said at least one neighboring light unit.

6. The method of claim 3 wherein said deriving step is performed by a first light unit, the first light unit not being in communication with a neighboring light unit which monitors at least part of the same geographical area as that being monitored by the first light unit; and
   further comprising the step of estimating the visibility conditions, pertaining to the geographical area being monitored by the first light unit, based on highest membership within the membership classes.

7. The method of claim 1 further comprising storing the following information on one or more databases accessible by a centralized server:
   a geographical location of each of the lighting devices and its associated visibility detector;
   a mapping of street locations associated with the lighting devices; and
   a direction and legal speed limit of traffic flow pertaining to the mapped street locations.

8. The method of claim 7 further comprising providing an early alert to drivers and to autonomous vehicles and devices approaching the area determined to have reduced visibility.

9. The method of claim 8 wherein said providing step comprises:
   determining one or more street locations where vehicles in said locations are approaching the determined area of reduced visibility.

10. A system for providing visibility alerts, said system comprising:
   at least one Outdoor Lighting Network (OLN) comprising a plurality of lighting units, at least two of which being in communication with each other;
   a plurality of visibility detectors, each in communication with at least one of the lighting devices, and each capable of monitoring a geographical area;
   a data analysis engine for receiving monitoring data from two or more of the visibility detectors and for deriving a consolidated estimate of visibility conditions pertaining to a combined geographical area defined by the monitored geographical areas associated with two or more visibility detectors, and determining direction and speed of area of reduced visibility area using the consolidated estimate of visibility conditions; and,
   a communication module for transmitting information pertaining to said estimated visibility conditions and/or area of reduced visibility.

11. The system of claim 10 wherein said data analysis engine comprises a means for mapping from data received from each visibility detector to a set of tuples; wherein said tuples comprises membership classes that are associated with levels of obscured visibility.

12. The system of claim 11 wherein said tuples comprises a percentage membership associated with each class.

13. The system of claim 12 wherein said data analysis engine resides in a centralized server; and wherein tuples from a plurality of light units are utilized in deriving the consolidated estimate.

14. The system of claim 12 wherein said data analysis engine resides in a first light unit, the first light unit being in communication with a least one neighboring light unit which monitors at least part of the same geographical area as that being monitored by the first light unit;
wherein an estimate derived by the first light unit pertaining to the geographical area being monitored by the first light unit is merged with one or more estimates obtained by said at least one neighboring light unit.

15. The system of claim 12 wherein said data analysis engine resides in a first light unit, the first light unit not being in communication with a neighboring light unit which monitors at least part of the same geographical area as that being monitored by the first light unit;
wherein an estimate of visibility conditions pertaining to the geographical area being monitored by the first light unit is derived by the first light unit based on highest membership within the membership classes.

16. The system of claim 10 further comprising:
a centralized server; and,
one or more databases, said databases comprising the following information:
a geographical location of each of the lighting devices and its associated visibility detector;
a mapping of street locations associated with the lighting devices; and
a direction and legal speed limit of traffic flow pertaining to the mapped street locations.

17. The system of claim 16 further comprising a means for providing an early alert to drivers approaching the area determined to have reduced visibility.

18. The system of claim 17 wherein the means for providing comprises:
means for determining one or more street locations where vehicles in said locations are approaching the determined area of reduced visibility.

19. The system of claim 17 wherein the means for providing an early alert are selected from the group consisting of:
communication means for communicating with a handheld communication device of the driver;
communication means for communicating by one or more light units directly with the driver's vehicle;
communication means for communicating from the centralized server to the driver's vehicle; and
communication means for communicating between vehicles themselves.

20. A computer program product comprising a plurality of program code portions, stored in a non-transitory computer readable medium, for carrying out the method according to claim 1.

21. A system for providing alerts pertaining to one or more environmental conditions, said system comprising:
at least one Outdoor Lighting Network (OLN) comprising a plurality of lighting units, at least two of which being in communication with each other;
a plurality of detectors, each in communication with at least one of the lighting devices, and each capable of monitoring an environmental condition associated with a geographical area;
a data analysis engine for receiving monitoring data from two or more of the visibility detectors and for deriving a consolidated estimate of said one or more environmental conditions pertaining to a combined geographical area defined by the monitored geographical areas associated with two or more detectors, and determining direction and speed of area of reduced visibility area using the consolidated estimate of visibility conditions; and,
a communication module for transmitting information pertaining to said estimated environmental conditions and/or area of reduced visibility.

22. The system of claim 21 wherein the environmental conditions being monitored are selected from the group consisting of flooding and reduced visibility conditions due to fog, smoke, and dust.

23. The method of claim 1 wherein the information pertaining to said estimated visibility conditions is selected from the group consisting of severity of fog occurring in an affected area, location of the fog, direction of movement of the fog, and speed of fog movement.

* * * * *